United States Patent
Bazin et al.

(10) Patent No.: US 6,413,526 B1
(45) Date of Patent: *Jul. 2, 2002

(54) COSMETIC AND/OR DERMATOLOGICAL COMPOSITION COMPRISING A DISPERSION OF A POLYMER SYSTEM, AND USE OF THIS SYSTEM AS A TENSIONING AGENT

(75) Inventors: Roland Bazin, Bievres; Laurent Bernardet, Villejuif; Didier Candau, Bievres; Gerard Malle, Villiers sur Morin; Jean-Claude Garson, Suresnes, all of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/348,167

(22) Filed: Jul. 7, 1999

Related U.S. Application Data

(63) Continuation-in-part of application No. 09/142,046, filed as application No. PCT/FR97/02461 on Dec. 30, 1997, now Pat. No. 6,001,367.

(30) Foreign Application Priority Data

Jan. 3, 1997 (FR) ............................................. 97/00033

(51) Int. Cl.⁷ .............................. A61K 6/00; A61K 7/00
(52) U.S. Cl. ..................... 424/401; 424/400; 424/195.1
(58) Field of Search ................................ 424/400, 401, 424/195.1

(56) References Cited

U.S. PATENT DOCUMENTS

| | | | |
|---|---|---|---|
| 3,463,862 A | 8/1969 | Mazza | |
| 3,471,624 A | 10/1969 | Youngblood | |
| 4,297,884 A | 11/1981 | Leveque et al. | |
| 4,360,537 A | 11/1982 | Tan et al. | |
| 5,100,658 A | 3/1992 | Bolich, Jr. et al. | |
| 5,443,855 A | 8/1995 | Wolf et al. | |
| 5,700,455 A | 12/1997 | Hinterwaldner et al. | |
| 5,776,917 A | * 7/1998 | Blank et al. | ................ 514/159 |
| 5,879,684 A | * 3/1999 | Fox | ......................... 424/195.1 |
| 6,001,367 A | * 12/1999 | Bazin et al. | ............. 424/195.1 |

FOREIGN PATENT DOCUMENTS

| | | |
|---|---|---|
| EP | 0 648 485 | 4/1995 |
| WO | 96/19180 | 6/1996 |
| WO | 98/29091 | 7/1998 |

OTHER PUBLICATIONS

Frei et al, International Journal of Cosmetic Science (1998), vol. 20, pp. 159–173.*

Tjahjadi, C., et al., "Isolation and Characterization of Adzuki Bean (*Vigna angularis cv Takara*) Proteins," *Journ. Of Food Sci.*, vol. 53, No. 5, pp. 1438–1443 (1988).

Rasseneur, L., et al., "Influence des differents constituants de la couche cornee sur la mesure do son élasticité," *Int'l Journ. Of Cosmetic Sci.*, 4, pp. 247–260 (1982).

* cited by examiner

Primary Examiner—Dameron L. Jones
(74) Attorney, Agent, or Firm—Oblon, Spivak, McClelland, Maier & Neustadt, P.C.

(57) ABSTRACT

The present invention relates to an anti-wrinkle composition containing a dispersion of a polymer system comprising at least one polymer of natural origin, and to the use of this polymer system as a tensioning agent in a cosmetic or dermatological composition.

The polymer used must characteristically have a molecular weight of greater than 670,000 daltons and the polymer system obtained must be capable of forming a steam-permeable film, it must have a Young's modulus ranging from $10^8$ to $9 \times 10^9$ N/m² and it must produce, at a concentration of 7%, a greater than 1.5% retraction of isolated stratum corneum at 30° C. and at a relative humidity of 40%.

The composition obtained is used in particular for the immediate treatment of wrinkles and fine lines on the skin.

30 Claims, No Drawings

COSMETIC AND/OR DERMATOLOGICAL COMPOSITION COMPRISING A DISPERSION OF A POLYMER SYSTEM, AND USE OF THIS SYSTEM AS A TENSIONING AGENT

This application is a continuation-in-part application of application Ser. No. 09/142,046, filed on Nov. 17, 1988, now U.S. Pat. No. 6,001,367, which is a 371 of PCT/FR97/02461 filed Dec. 30, 1997.

The present invention relates to an anti-wrinkle composition containing a polymer system comprising at least one polymer of natural origin, and to the use of this polymer system as a tensioning agent in a cosmetic composition or for the manufacture of a dermatological composition, which are intended in particular for the treatment, reduction, elimination and/or smoothing-out of wrinkles and fine lines on human skin.

In the course of the ageing process, different signs appear on the skin, which are very characteristic of this ageing, reflected in particular by a change in the skin's structure and functions. The main clinical signs of ageing of the skin are, in particular, the appearance of fine lines and deep wrinkles, which increase with age. Disorganization of the skin's "grain" is observed in particular, i.e. the microrelief is less uniform and has an anisotropic nature.

It is known to treat these signs of ageing using cosmetic or dermatological compositions containing active agents that are capable of combating ageing, such as α-hydroxy acids, β-hydroxy acids and retinoids. These active agents act on wrinkles by removing the dead cells from the skin and by accelerating the process of cell renewal. However, these active agents have the drawback of being effective for the treatment of wrinkles only after they have been applied for a certain period. Now, it is increasingly sought to obtain an immediate effect with the active agents used, leading rapidly to a smoothing out of wrinkles and fine lines and the disappearance of fatigue marks.

The subject of the present invention is, precisely, the use of a specific polymer system which makes it possible to obtain this effect immediately.

The Applicant has discovered that certain polymers of natural origin have defined physical characteristics and constitute particularly effective tensioning agents. The term "tensioning agent" is understood to refer to compounds capable of having a tensioning effect, i.e. capable of stretching the skin and, by means of this tensioning effect, making the skin smooth and immediately reducing the wrinkles and fine lines on it, or even making them disappear altogether.

In order to be effective, the polymers used according to the invention must have well defined characteristics, and in particular must have a molecular weight of greater than 670,000 daltons, which means that at least a fraction of the polymer has a molecular weight of greater than 670,000 daltons. Moreover, the polymer systems used according to the invention must be capable of forming a steam-permeable film, they must have a Young's modulus ranging from $10^8$ to $9 \times 10^9$ N/m$^2$ and they must produce, at a concentration of 7% in water, a greater than 1.5% retraction of isolated stratum corneum at 30° C. and at a relative humidity of 40%.

Thus, the subject of the present invention is the use of at least one dispersion of a polymer system containing at least one polymer of natural origin having a molecular weight of greater than 670,000 daltons, the said polymer system being capable of forming a steam-permeable film, having a Young's modulus ranging from $10^8$ to $9 \times 10^9$ N/m$^2$ and producing, at a concentration of 7% in water, a greater than 1.5% retraction of isolated stratum corneum at 30° C. and at a relative humidity of 40%, in a cosmetic composition for reducing and/or eliminating wrinkles and/or fine lines on the skin by means of a tensioning effect.

The subject of the present invention is also the use of at least one dispersion of a polymer system containing at least one polymer of natural origin having a molecular weight of greater than 670,000 daltons, the said polymer system being capable of forming a steam-permeable film, having a Young's modulus ranging from $10^8$ to $9 \times 10^9$ N/m$^2$ and producing, at a concentration of 7% in water, a greater than 1.5% retraction of isolated stratum corneum at 30° C. and at a relative humidity of 40%, as a tensioning agent in a cosmetic composition in order to reduce and/or eliminate wrinkles and/or fine lines on the skin.

The subject of the present invention is also the use of at least one dispersion of a polymer system containing at least one polymer of natural origin having a molecular weight of greater than 670,000 daltons, the said polymer system being capable of forming a steam-permeable film, having a Young's modulus ranging from $10^8$ to $9 \times 10^9$ N/m$^2$ and producing, at a concentration of 7% in water, a greater than 1.5% retraction of isolated stratum corneum at 30° C. and at a relative humidity of 40%, for the manufacture of a dermatological composition intended to eliminate wrinkles and/or fine lines on the skin by means of a tensioning effect.

The invention also relates to a process for the cosmetic treatment of wrinkled skin, which consists in applying to the wrinkles at least one dispersion of a polymer system containing at least one polymer of natural origin having a molecular weight of greater than 670,000 daltons, the said polymer system being capable of forming a steam-permeable film, having a Young's modulus ranging from $10^8$ to $9 \times 10^9$ N/m$^2$ and producing, at a concentration of 7% in water, a greater than 1.5% retraction of isolated stratum corneum at 30° C. and at a relative humidity of 40%, in an amount which is effective for eliminating the wrinkles by means of a tensioning effect.

The invention also relates to an anti-wrinkle composition, characterized in that it contains, in a medium which is physiologically acceptable on the skin for several hours, at least one dispersion of a polymer system containing at least one polymer of natural origin having a molecular weight of greater than 670,000 daltons, the said polymer system being capable of forming a steam-permeable film, having a Young's modulus ranging from $10^8$ to $9 \times 10^9$ N/m$^2$ and producing, at a concentration of 7% in water, a greater than 1.5% retraction of isolated stratum corneum at 30° C. and at a relative humidity of 40%.

The polymer system used according to the present invention has the property of eliminating, immediately after application, the wrinkles and fine lines on the surface of the skin. The composition of the invention is more especially suited to application to the face and the neck, in particular the neckline.

The term "polymer system" is understood to refer either to a polymer alone or to a polymer combined with at least one other polymer or to a polymer combined with at least one plasticizer so as to obtain the desired mechanical properties.

The expression "capable of forming a film" is understood to refer to a polymer system which allows a film to be formed: when it is spread onto glass, the polymer system must dry without becoming individualized like a film of lacquer.

The term "water-permeable" is understood to refer to a film which is porous to steam. The permeability of the film is demonstrated by measuring the IWL (imperceptible water loss) of defatted stratum corneum treated with the polymer system. When the film is steam-porous, the IWL is not modified by the film. The IWL is conventionally measured using an evaporimeter (Servomed) which quantitatively determines water evaporation, i.e. transportation of water by diffusion, using a sample of stratum corneum which closes off a cylindrical capsule containing water, the assembly being placed in a chamber at controlled temperature and relative humidity. Sensors allow the partial pressure of water vapor to be measured at two points located at different distances from the sample. The water vapor partial pressure gradient between the two points is thus determined, and hence the degree of evaporation in accordance with Fick's law.

As indicated above, the polymer system used according to the invention has a Young's modulus ranging from $10^8$ to $9 \times 10^9$ N/m$^2$, determined by instrumented indentation methods (micro- or nanoindentation; ASTM standard E384-89), which corresponds to a modulus of elasticity at least 10 to 100 times as high as that of the stratum corneum. The use of a polymer system having such a Young's modulus makes it possible to obtain both immediate and persistent efficacy and good comfort in the tensioning effect, i.e. without excessive tautness.

In addition, the polymer system used according to the invention produces, at a concentration of 7% in water, a greater than 1.5% retraction of isolated stratum corneum at 30° C. and at a relative humidity of 40%. This retraction is measured with a Dermometer.

The Dermometer is described in Rasseneur L. et al, Influence des Différents Constituants de la Couche Cornée sur la Mesure de son Elasticité, *International Journal of Cosmetic Science*, 4, 247–260 (1982), and is covered by U.S. Pat. No. 4,297,884.

The retraction is measured according to the following method.

The principle on which the method is based consists in measuring the length of a sample of stratum corneum on a Dermometer, both before and after treatment with a solution containing the polymer to be tested.

The sample of stratum corneum can be isolated from a piece of human skin resulting from plastic surgery.

The method comprises the following steps:
1. The sample of stratum corneum is placed between the two jaws of the Dermometer, one of which is fixed and the other of which is movable, in an atmosphere at 30° C. and 40% of relative humidity.
2. The sample of stratum corneum is drawn and the strength (in grams) is plotted against the length (in millimeter), wherein the zero length corresponds to the contact between the jaws.
3. The tangent to the linear part of the curve thus obtained is then drawn. The meeting point of the tangent with the axis of the lengths corresponds to the apparent length $L_0$ of the sample at a zero force.
4. The sample is then relaxed, and 2 mg/cm$^2$ of the solution to be tested are applied thereto.
5. After 15 min of drying, steps 1–4 described above are repeated to obtain the apparent length $L_1$ of the sample as treated.
6. The percentage of reaction is defined as:

$$\% \text{ retraction} = 100 \times (L_1 - L_0)/L_0.$$

To characterize a tensioning effect of the polymer, this percentage should be negative and the tensioning effect is in proportion to the absolute value of the percentage of retraction.

Admittedly, it is known to use polymers, and in particular certain proteins, for their tensioning effect. Thus, document EP-A-180,968 describes a composition for treating wrinkles which contains human serum albumin. However, the Applicant has found that specific polymers had a higher efficacy than those of the prior art, in particular on account of the much longer-lasting tensioning effect obtained.

Patent application WO 96/19180 describes skin-firming compositions comprising a film-forming agent containing at least one plant polysaccharide and hydrolyzed casein as tensioning active agents. However, the natural polymers described in that patent application do not satisfy the characteristics of the polymers according to the present invention and they do not allow satisfactory retraction of the stratum corneum to be obtained.

U.S. Pat. No. 3,471,624 describes compositions intended for skin care, in particular, for smoothing out wrinkles, these compositions comprising methylcellulose as stabilizer. That document does not at all disclose the use of cellulose derivatives as tensioning agents.

The polymers according to the invention allow a tensioning effect to be obtained effectively for more than three hours, this effect being very well tolerated by the user (comfortable and not taut).

The expression "polymer of natural origin" is understood to refer to polymers of plant origin, polymers derived from the exoskeleton and latices of natural origin. These polymers are preferably hydrophilic.

As polymers of plant origin, mention may be made in particular of proteins and protein hydrolyzates, and more particularly extracts of cereals, of leguminous plants and of oleaginous plants, such as extracts of corn, rye, *Triticum aestivum*, buckwheat, sesame, *Triticum spelta*, pea, bean, lentil, soybean and lupin. These polymers of plant origin must have at least one fraction with a molecular weight of greater than 670,00 daltons. As suitable proteins, mention may be made, for example, of the soybean protein extract sold by the company ISD under the name "Profam 972" and the protein fraction of white lupin.

Methods for extracting plant proteins are well-known in the art and are disclosed, for example, in WO94/65640; U.S. Pat. Nos. 4,089,848; 4,208,259; and 4,407,841.

Any polymer derived from body hair, nails, insect or crustacean carapaces, head hair, feathers, beaks or animal hooves or horns can be used as exoskeleton-derived polymers. Mention may be made, for example, of chitin and its derivatives, in particular chitosan which is a deacetyl derivative of chitin, as well as chitosan derivatives such as hydroxypropylchitosan, the succinyl derivative of chitosan, chitosan lactate, chitosan glutamate and carboxymethylchitosan succinamide; keratin derivatives such as keratin hydrolyzates and sulphonic keratins.

The polymers of natural origin, which are optionally modified, consisting of latices, can be chosen, for example, from shellac resin, sandarac gum, dammar resins, elemi gums, copal resins and cellulose derivatives, and mixtures thereof.

The plasticizer which may be present can be chosen from any compound known to those skilled in the art as being capable of fulfilling the desired function. This agent can be water-soluble or water-insoluble and can optionally be in the form of an aqueous dispersion.

In particular, mention may be made, alone or as a mixture, of the usual plasticizers, such as glycols and their derivatives such as diethylene glycol ethyl ether or methyl ether, ethylene glycol ethyl ether or butyl ether, propylene glycol methyl ether or phenyl ether, dipropylene glycol ethyl ether or butyl ether, tripropylene glycol butyl ether or methyl ether; glycerol esters; acid esters such as citrates, phthalates, adipates, carbonates, tartrates, phosphates, sebacates; oxyethylenated derivatives such as oxyethylenated oils, in particular plant oils such as oxyethylenated castor oil and oxyethylenated silicone oils; water-soluble polymers or polymers in aqueous dispersion, having a low glass transition temperature, of less than 25° C., preferably less than 15° C. Mention may also be made of polysaccharides, and in particular carrageenan gum, xanthan gum and gum arabic.

The amount of plasticizer is chosen by a person skilled in the art on the basis of his or her general knowledge, so as to obtain a polymer system which leads to a film having the desired mechanical properties, while at the same time retaining the composition's cosmetically acceptable properties.

The polymer system used (polymer(s) or polymer and plasticizer) according to the invention can be present in particular in an active material (A.M.) amount ranging from 0.5 to 70%, and better still from 0.5 to 30%, of the total weight of the composition.

The composition containing the polymer system used according to the invention can comprise, besides the dispersion of polymer of natural origin, an aqueous dispersion of at least one polymer of synthetic origin and in particular a synthetic polymer in the form of a latex or a pseudolatex.

The latices result directly from the synthesis of a polymer by a well-known emulsion polymerization technique. The optional neutralization of the latex is such that the polymer remains in latex form and does not dissolve in the water. Such latices are used, for example, in nail varnishes (see EP-A-648,485).

In order to obtain a pseudolatex, a polymer is prepared and is then dispersed in water. The dispersion in water is self-stabilized by at least partial neutralization of the acid groups borne by the polymer.

The latex or pseudolatex particles preferably have a size ranging from 10 to 400 nm and preferably from 20 to 350 nm.

The synthetic polymers of the latices or pseudolatices can be of polycondensate type or of radical type.

As polycondensates, mention may be made of anionic, cationic, nonionic or amphoteric polyurethanes, polyurethane-acrylics, polyurethane-polyvinylpyrrolidones, polyester-polyurethanes, polyether-polyurethanes and polyureas, and mixtures thereof.

The polyurethane can be, for example, an aliphatic, cycloaliphatic or aromatic, polyurethane, polyurea/urethane or polyurea copolymer. The polyurethanes can also be obtained from branched or unbranched polyesters, or from alkyds containing labile hydrogens, which are modified by reaction with a diisocyanate and a difunctional (for example dihydro, diamino or hydroxyamino) organic compound also containing either a carboxylic acid or carboxylate group, or a sulphonic acid or sulphonate group, or alternatively a neutralizable tertiary amine group or a quaternary ammonium group. Mention may also be made of polyesters, polyesteramides, fatty-chain polyesters, polyamides and epoxyester resins.

These polymers are, in particular, those described in document EP-A-648,485.

The latices or pseudolatices can also consist of acrylic polymers, acrylic copolymers (CTFA name=acrylate copolymers) and sulphonated isophthalic acid polymers.

The latices or pseudolatices can also be obtained from polymers resulting from the radical polymerization of one or more radical monomers inside and/or partially at the surface of pre-existing particles of at least one polymer chosen from the group consisting of polyurethanes, polyureas, polyesters, polyesteramides and/or alkyds. These polymers are generally referred to as hybrid polymers.

As synthetic polymers which are suitable for use with the tensioning agent according to the invention, mention may be made in particular of dispersions of polyester-polyurethane and of polyether-polyurethane, sold under the names "Sancure 2060" (polyesterpolyurethane), "Sancure 2255" (polyesterpolyurethane), "Sancure 815" (polyesterpolyurethane), "Sancure 878", (polyetherpolyurethane) and "Sancure 861" (polyether-polyurethane), by the company Sanncor, under the names "Neorez R974" (polyesterpolyurethane), "Neorez R981" polyesterpolyurethane) and "Neorez R970" (polyether-polyurethane), by the company ICI, and the acrylic copolymer dispersion sold under the name "Neocryl XK-90", by the company Zeneca.

The synthetic polymer dispersion can be present in an active material amount preferably ranging from 0.5 to 50% of the total weight of the composition, and preferably from 0.5 to 25% of the total weight of the composition, the total amount of the polymer system being that indicated above.

According to the present invention, the composition containing the polymer system is suitable for topical use and thus contains a physiologically acceptable medium, i.e. one which is compatible with the skin for several hours. The term "several hours" is understood to mean at least two hours and preferably more than three hours.

The pH of the composition is close to the pH of the skin, i.e. from about 5 to about 8 and preferably 5.5 to 6.5.

The composition of the invention can be in any pharmaceutical form normally used for topical application, in particular in the form of an aqueous, aqueous-alcoholic or oily solution, an oil-in-water or water-in-oil or multiple emulsion, an aqueous or oily gel a liquid, pasty or solid anhydrous product, a dispersion of oil in an aqueous phase in the presence of spherules, it being possible for these spherules to be polymer nanoparticles such as nanospheres and nanocapsules or better still lipid vesicles of ionic and/or nonionic type.

This composition can be more or less fluid and can have the appearance of a white or colored cream, an ointment, a milk, a lotion, a serum, a paste or a mousse. It can optionally be applied to the skin in aerosol form. It can also be in solid form and, for example, in stick form. It can be used as a care product and/or as a make-up product for the skin.

The composition of the invention more particularly constitutes an anti-wrinkle composition, in particular in the form of a serum.

In a known manner, the composition of the invention can also contain adjuvants that are common in the cosmetics and dermatological fields, such as hydrophilic or lipophilic gelling agents, hydrophilic or lipophilic active agents, preserving agents, antioxidants, solvents, fragrances, fillers, screening agents, pigments, odor absorbers and dyestuffs. The amounts of these various adjuvants are those used conventionally in the fields considered, and, for example, from 0.01 to 20% of the total weight of the composition. Depending on their nature, these adjuvants can be introduced into the fatty phase, into the aqueous phase, into the lipid vesicles and/or into the nanoparticles. These adjuvants and their concentrations must be such that they do not modify the desired tensioning property of the polymer system.

When the composition of the invention is an emulsion, the proportion of the fatty phase can range from 5 to 80% by weight, and preferably from 5 to 50% by weight, relative to the total weight of the composition. The fatty substances, the emulsifiers and the co-emulsifiers used in the composition in emulsion form are chosen from those used conventionally in the field considered. The emulsifier and the co-emulsifier are preferably present in the composition in a proportion ranging from 0.3 to 30% by weight, and preferably from 0.5 to 20% by weight, relative to the total weight of the composition.

As fatty substances which can be used in the invention, mention may be made of oils and in particular mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids, waxes and gums and in particular silicone gums can also be used as fatty substances.

As emulsifiers and co-emulsifiers which can be used in the invention, mention may be made, for example, of fatty acid esters of polyethylene glycol, such as PEG-50 stearate and PEG-40 stearate, and fatty acid esters of polyol such as glyceryl stearate and sorbitan tristearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and as lipophilic gelling agents, mention may be made of modified clays such as bentones, metal salts of fatty acids, hydrophobic silica and polyethylenes.

Polyols (glycerol, propylene glycol), vitamins, keratolytic agents and/or desquamating agents (salicylic acid and its derivatives, α-hydroxy acids, ascorbic acid and its derivatives), anti-inflammatory agents and calmants, and mixtures thereof, can be used in particular as active agents. Active agents capable of combating ageing in the longer term, and in particular α-hydroxy acids, β-hydroxy acids and retinoids, can in particular be incorporated into the composition according to the invention; these active agents complement the effect of the tensioning agents according to the invention. As α-hydroxy acids, mention may be made in particular of glycolic acid, lactic acid, malic acid, tartaric acid, citric acid and mandelic acid. As β-hydroxy acids, mention may be made of salicylic acid and its derivatives, 2-hydroxy-alkanoic acids and their derivatives such as 2-hydroxy-3-methylbenzoic acid and 2-hydroxy-3-methoxybenzoic acid. As retinoids, mention may be made of retinol and its esters (palmitate, acetate, propionate), as well as retinoic acid and its derivatives.

In addition, the tensioning agents used according to the invention can also be combined with other compounds known to those skilled in the art as tensioning agents which have different properties from those of the agents used according to the invention, in particular a protein or protein hydrolyzate. As compounds of this type, mention may be made, for example, of milk proteins such as lactalbumin, plant proteins such as the soybean protein sold under the name Eleseryl by the company LSN, or the oat derivative sold under the name "Reductine" by the company Silab, and nucleic acids such as DNA.

In the event of incompatibility, the active agents mentioned above can be incorporated into spherules, in particular ionic or nonionic vesicles and/or nanoparticles (nanocapsules and/or nanospheres), so as to isolate them from each other in the composition.

The examples below of compositions according to the invention are given by way of illustration and with no limiting nature. The amounts therein are given as a % by weight.

EXAMPLE 1

Anti-wrinkle Serum

| | |
|---|---|
| Soybean protein (Profam 972 sold by the company ISD) | 7% |
| Preserving agent | 0.3% |
| Demineralized water qs | 100% |

EXAMPLE 2

Anti-wrinkle Cream

| | |
|---|---|
| Cetyl alcohol | 7% |
| Liquid petroleum jelly | 9% |
| Diglyceryl stearate | 2.5% |
| PEG-50 stearate | 2.5% |
| Sodium hydroxide qs pH | 8 |
| Protein fraction of white lupin, containing 0.7% A.M. | 40% |
| Demineralized water qs | 100% |

EXAMPLE 3

Lotion

| | |
|---|---|
| Sancure 878 containing 33% A.M. | 85% |
| Soybean protein (Profam 972 sold by the company ISD) | 6% |
| Xanthan gum | 5% |
| Glycerol | 1.5% |
| Demineralized water qs | 100% |

EXAMPLE 4

Anti-wrinkle Cream

| | |
|---|---|
| Cetyl alcohol | 4% |
| Liquid petroleum jelly | 8% |
| Sorbitan tristearate | 0.9% |
| PEG-40 stearate | 2% |
| Glyceryl stearate | 3% |
| Plant oil | 4% |
| Cyclomethicone | 5% |
| Soybean protein (Profam 972 sold by the company ISD) | 7% |
| Sancure 2060 containing 40% A.M. | 20% |
| Demineralized water qs | 100% |

EXAMPLE 5

Anti-wrinkle Cream

| | |
|---|---|
| Cetyl alcohol | 4% |
| Liquid petroleum jelly | 8% |
| Sorbitan tristearate | 0.9% |
| PEG-40 stearate | 2% |
| Glyceryl stearate | 3% |
| Plant oil | 4% |

-continued

| Cyclomethicone | 5% |
| --- | --- |
| Succinyl derivative of chitosan | 7% |
| Sancure 2060 containing 40% A.M. | 20% |
| Demineralized water qs | 100% |

The disclosure of U.S. application Ser. No. 09/142,046, filed Nov. 17, 1998, is hereby incorporated by reference.

What is claimed is:

1. A cosmetic method for reducing and/or eliminating wrinkles and/or fine lines on the skin by means of a tensioning effect comprising applying to the skin at least one dispersion of a polymer system containing at least one polymer of natural origin selected from the group consisting of (1) polymers of plant origin selected from the group consisting of extracts of cereals, of leguminous plants and of oleaginous plants, (2) polymers derived from the exoskeleton and (3) latices of natural origin, said polymer of natural origin having a molecular weight of greater than 670,000 daltons, the said polymer system which forms a steam-permeable film, having a Young's modulus ranging from $10^8$ to $9 \times 10^9$ N/m$^2$ and producing, at a concentration of 7% in water, a greater than 1.5% retraction of isolated stratum corneum at 30° C. and at a relative humidity of 40%, wherein when the polymer of natural origin is from group (1), the extract is selected from the group consisting of extracts of corn, rye, *Triticum aestivum,* buckwheat, sesame, Triticum spelta, bean, lentil, soybean and lupin.

2. The method of claim 1, wherein the polymer is a hydrophilic polymer.

3. The method of claim 1, wherein the polymer of natural origin is selected from the group consisting of shellac resin, sandarac gum, dammar resins, elemi gums, copal resins and cellulose, and mixtures thereof.

4. The method of claim 1, wherein the polymer of natural origin is selected from the group consisting of extracts of cereals, of leguminous plants and of oleaginous plants, and mixtures thereof.

5. The method of claim 1, wherein the polymer system also comprises a plasticizer.

6. The method of claim 1, wherein the polymer system is present in an active material amount ranging from 0.5 to 70% of the total weight of the composition.

7. The method of claim 6, wherein the polymer system is present in an active material amount ranging from 0.5 to 30% of the total weight of the composition.

8. The method of claim 1, wherein the composition also contains an aqueous dispersion of at least one polymer of synthetic origin.

9. The method of claim 8, wherein the dispersion of polymer of synthetic origin is a latex or a pseudolatex.

10. The method of claim 9, wherein the polymer of synthetic origin is selected from the group consisting of anionic, cationic, nonionic and amphoteric polyurethanes, polyurethane-acrylics, polyurethane-polyvinylpyrrolidones, polyester, polyurethanes, polyether-polyurethanes, polyureas, acrylic polymers and copolymers, and sulphonated isophthalic acid polymers, and mixtures thereof.

11. The method of claim 1, wherein the composition contains a medium which is physiologically acceptable to the skin for several hours.

12. The method of claim 1, wherein the composition is in the form of a serum.

13. The method of claim 1, wherein the composition also contains at least one adjuvant selected from the group consisting of hydrophilic and lipophilic gelling agents, hydrophilic and lipophilic active agents, preserving agents, antioxidants, solvents, fragrances, fillers, screening agents, pigments, odor absorbers and dyestuffs.

14. The method of claim 1, wherein the composition also contains at least one active agent selected from the group consisting of α-hydroxy acids, β-hydroxy acids and retinoids.

15. An anti-wrinkle composition comprising, in a medium which is physiologically acceptable for several hours on the skin, at least one dispersion of a polymer system containing at least one polymer of natural origin selected from the group consisting of (1) polymers of plant origin selected from the group consisting of extracts of cereals, of leguminous plants and of oleaginous plants, (2) polymers derived from the exoskeleton and (3) latices of natural origin, said polymer of natural origin having a molecular weight of greater than 670,000 daltons, the said polymer system which forms a steam-permeable film, having a Young's modulus ranging from $10^8$ to $9 \times 10^9$ N/m$^2$ and producing, at a concentration of 7% in water, a greater than 1.5% retraction of isolated stratum corneum at 30° C. and at a relative humidity of 40%, wherein the extract is selected from the group consisting of extracts of corn, rye, *Tricitum aestivum*, buckwheat, sesame, *Triticum spelta*, bean, lentil, soybean and lupin.

16. The composition of claim 15, wherein the polymer is a hydrophilic polymer.

17. The composition of claim 15, wherein the polymer of natural origin is selected from the group consisting of shellac resin, sandarac gum, dammar resins, elemi gums, copal resins and cellulose, and mixtures thereof.

18. The composition of claim 15, wherein the polymer of natural origin is selected from the group consisting of extracts of cereals, of leguminous plants and of oleaginous plants, and mixtures thereof.

19. The composition of claim 15, wherein the polymer system also comprises a plasticizer.

20. The composition of claim 15, wherein the polymer system is present in an active material amount ranging from 0.5 to 70% of the total weight of the composition.

21. The composition of claim 20, wherein the polymer system is present in an active material amount ranging from 0.5 to 30% of the total weight of the composition.

22. The composition of claim 15, wherein the composition also contains an aqueous dispersion of at least one polymer of synthetic origin.

23. The composition of claim 22, wherein the dispersion of polymer of synthetic origin is a latex or a pseudolatex.

24. The composition of claim 23, wherein the polymer of synthetic origin is selected from the group consisting of anionic, cationic, nonionic and amphoteric polyurethanes, polyurethane-acrylics, polyurethane-polyvinylpyrrolidones, polyester, polyurethanes, polyether-polyurethanes, polyureas, acrylic polymers and copolymers, and sulphonated isophthalic acid polymers, and mixtures thereof.

25. The composition of claim 15, wherein the composition contains a medium which is physiologically acceptable to the skin for several hours.

26. The composition of claim 15, wherein the composition is in the form of a serum.

27. The composition of claim 15, wherein the composition also contains at least one adjuvant selected from the group consisting of hydrophilic and lipophilic gelling agents, hydrophilic and lipophilic active agents, preserving agents, antioxidants, solvents, fragrances, fillers, screening agents, pigments, odor absorbers and dyestuffs.

28. The composition of claim 15, wherein the composition also contains at least one active agent selected from the group consisting of α-hydroxy acids, β-hydroxy acids and retinoids.

29. The method of claim 1, wherein the polymer is chitosan or a derivative thereof.

30. The composition of claim 15, wherein the polymer is chitosan or a derivative thereof.

* * * * *

UNITED STATES PATENT AND TRADEMARK OFFICE
CERTIFICATE OF CORRECTION

PATENT NO.    : 6,413,526 B1
DATED         : July 2, 2002
INVENTOR(S)   : Roland Bazin et al.

It is certified that error appears in the above-identified patent and that said Letters Patent is hereby corrected as shown below:

Column 9,
Line 15, "dispersion of a polymer system containing at least one" should read
-- dispersion of a polymer system containing a wrinkle and/or fine line reducing and/or eliminating effective amount of at least one --.

Column 10,
Line 11, "skin, at least one dispersion of a polymer system containing" should read
-- skin, at least one dispersion of a polymer system containing a wrinkle and/or fine line reducing and/or eliminating effective amount of --.
Line 24, "*Tricitum*" should read -- *Triticum* --.

Signed and Sealed this

Twelfth Day of August, 2003

JAMES E. ROGAN
*Director of the United States Patent and Trademark Office*